United States Patent [19]

Laufenberg et al.

[11] 4,454,873

[45] Jun. 19, 1984

[54] SEPARATOR MEDIUM FOR ORTHOPEDIC CAST MATERIAL

[75] Inventors: Carol J. Laufenberg, Pleasanton; Milton F. Custer, Byron, both of Calif.

[73] Assignee: Hexcel Corporation, San Francisco, Calif.

[21] Appl. No.: 352,921

[22] Filed: Feb. 26, 1982

[51] Int. Cl.³ .............................................. A61F 5/04
[52] U.S. Cl. .................................................. 128/90
[58] Field of Search ........................... 128/90, 89, 156; 427/389–392; 428/264–268, 481–483

[56] References Cited

U.S. PATENT DOCUMENTS

| | | | |
|---|---|---|---|
| 4,044,761 | 8/1977 | Hall | 128/90 |
| 4,105,025 | 8/1978 | Wang et al. | 128/90 |
| 4,214,578 | 7/1980 | Gianakakos et al. | 128/90 |
| 4,326,509 | 4/1982 | Usukura | 128/90 |
| 4,344,423 | 8/1982 | Evans et al. | 128/90 |
| 4,372,311 | 2/1983 | Potts | 128/156 |

*Primary Examiner*—John D. Yasko
*Attorney, Agent, or Firm*—John L. McGannon

[57] ABSTRACT

An orthopedic cast material having a thermoplastic material and provided with a quantity of (poly)ethylene oxide applied thereto to prevent adherence of adjacent convolutions of the cast material when it is in the form of a roll and is immersed in hot water prior to being wrapped on a limb or body part of a patient. The (poly)ethylene oxide can be in the form of a coating on the outer surface of the cast material or in the resin of the cast material.

17 Claims, No Drawings

SEPARATOR MEDIUM FOR ORTHOPEDIC CAST MATERIAL

BACKGROUND OF THE INVENTION

Thermoplastic materials forming orthopedic casts for wrapping limbs and other human body parts have been known and used in the past. A representative material of this type is one known as HEXCELITE and is made and sold by Hexcel Corporation, Dublin, Calif. Such a material is disclosed in U.S. Pat. No. 4,273,115. The material includes a large mesh, flexible fabric carrier, typically a cotton knit material, impregnated with a polyester polymer to provide a relatively thick coating of the polymer on the knit material while retaining substantially large openings in the mesh or fabric of the knit material. The cast material made in this manner is somewhat flexible and is capable of being wound into a roll to form a cylindrical package for storage until it is ready for use.

When the cast material is to be used, it is heated to a temperature above the softening point of the polymer or until the cast material softens to a flexible or pliable condition. Then the cast material can be readily molded or wrapped on the limb or body part of a patient. The softening of the cast material is achieved by immersing it in hot water. Upon being removed from the water, the cast material is wrapped immediately on the limb or body part, and the convolutions of the wrapped cast material bond to each other to form a unitary cast having high strength characteristics yet the cast is lightweight in construction, is abrasive and shock resistant, and is porous to permit air circulation therethrough.

A problem associated with orthopedic cast material of this type is the fact that the convolutions of the material adhere to each other when the cast material is being heat softened in hot water. Separating the convolutions then becomes difficult because the resin, when heated, adheres strongly to anything which it engages.

This problem has been overcome in the past by providing a plastic separator sheet between the convolutions of the cast material. The plastic of the separator sheet is generally unaffected by the hot water. Thus, the convolutions do not engage each other during the heat softening of the cast material. The separator sheet is removed from the cast material during the wrapping of the cast material or a limb or body part. Such a separator sheet is one of the type disclosed in U.S. Pat. No. 4,143,655. A separator sheet of this type is relatively high in cost and is hard to handle when the cast material is being wrapped onto a limb or a body part. Also, the separator sheet has a tendency to retain hot water which drips onto the patient and causes discomfort during the wrapping process.

Because of the aforesaid drawbacks of conventional separator sheets for orthopedic cast material of the type described, a need has arisen for improvements in the means and techniques for keeping adjacent convolutions of a roll of orthopedic cast material separated from each other during immersion of the role in hot water to thereby permit such cast material to be readily heated and then quickly wrapped onto the limb or body part of a patient.

DESCRIPTION OF THE PRIOR ART

In Chemical Abstracts 87:75066K (1977), a release coating is disclosed for use with paper, plastic film, fabric and the like. The coating is comprised of a mixture of a polysiloxane, ethylcellulose and poly(oxyethylene). Poly(oxyethylene) is yet another term equivalent to polyethylene glycol. The ethylcellulose and poly(oxyethylene) form from 0.5 to 20% of the composition of the mixture and the poly(oxyethylene) comprises approximately 7% of the mixture.

U.S. Pat. No. 3,420,231 discloses a release coating for a thermoplastic cast material. The coating is an inversely soluble resin having decreasing solubility with increasing temperature so that the degree of adherence of adjacent sheets decreases as the temperature is increased. The particular resins disclosed in this patent are methylcellulose, polyvinyl methyl ether, hydroxy propyl methyl cellulose, and certain copolymers of normal isopropyl acrylamide.

U.S. Pat. No. 4,107,380 discloses a coating for heat sealable films, typically foil or cellophane, having a waxy layer to achieve the heat sealing characteristic. A coating of an ethyl-vinyl acetate copolymer acts as a release agent to prevent sticking of the films when rolled.

U.S. Pat. Nos. 3,662,057 and 4,226,230 disclose thermal plastic cast material and U.S. Pat. Nos. 3,551,538 and 4,019,505 disclose polyethylene oxide film and polyethylene film, respectively.

SUMMARY OF THE INVENTION

The present invention satisfies the need for improvements in the means and techniques for keeping the convolutions of orthopedic cast material separated from each other during immersion in hot water. To this end, the invention is directed to the use of a release material on or in the body of a thermoplastic cast material suitable for orthopedic applications. The purpose of the release material is to prevent the attachment of the adjacent convolutions of the orthopedic cast material to each when the cast material, in the form of a roll, is immersed in hot water to soften it prior to being wrapped. The release material effectively prevents a mechanical or chemical bond between the layers of resin on adjacent convolutions, yet the cast material, when heated to the proper temperature can be quickly wrapped on a limb or body part and the adjacent convolutions will then bond to each other to form a unitary body of lightweight construction and one which is air pervious and highly resistant to abrasion and shock.

The material forming the release layer of the present invention is a water soluble (poly)ethylene oxide. A 0.01% to 0.5%, preferably 0.09%, by weight water solution of (poly)ethylene oxide is satisfactory for this purpose. A chlorinated solvent, such as methylene chloride, can be used in place of water.

A suitable commercial product comprised of (poly)ethylene oxide and useable for the purposes of the present invention is one known as POLYOX, a water soluble (poly)ethylene oxide made by Union Carbide Corporation. A family of (poly)ethylene oxide products is covered under the name POLYOX. The molecular weights of these products range between 100,000 and 4 million. The POLYOX product preferred for carrying out the teachings of the present invention has a molecular weight of about 400,000.

The (poly)ethylene oxide layer of the present invention is externally applied to the orthopedic cast material and allowed to dry. The (poly)ethylene oxide can be applied by dipping the orthopedic cast material into a solution of the (poly)ethylene oxide or the (poly)ethylene oxide can be sprayed onto the outer surface of the orthopedic cast material. A first variation of the present invention is the addition of 1% by weight of (poly)ethylene oxide to the resin of the orthopedic cast material to provide release properties therefor. A second variation is to use a coating of (poly)ethylene oxide on the outer surface of the cast material and a quantity of (poly)ethylene oxide in the resin of the cast material.

Since the (poly)ethylene oxide is water soluble, the (poly)ethylene oxide layer essentially breaks up as a surface layer when the orthopedic cast material, in roll form, is immersed in the hot water for a limited period of time to soften the cast material. Water is considered to be hot if it is in the range of 140°–180° F. for the particular resin of the cast material. The (poly)ethylene oxide is probably not completely removed from the outer surfaces of the cast material during this immersion step since sufficient (poly)ethylene oxide remains on the cast material to prevent adherence of adjacent convolutions of the cast material at least for the limited time, typically up to 30 minutes at 150° F., in which the cast material is in the hot water.

Upon being removed from the hot water, the cast material is then immediately wrapped upon a limb or body part of a patient. Even though a small amount of the (poly)ethylene oxide may remain on the cast material, the convolutions of the cast material adhere to each other and become bonded so as to form a unitary cast body having the aforesaid desirable strength and abrasion characteristics.

Methyl cellulose can be added to the resin of the cast material as a low viscosity tackifier. A non-ionic surfactant can be added to the (poly)ethylene oxide as a wetting agent. Talc can be added to the resin to reduce tack.

What is claimed is:

1. An assembly for use as an orthopedic cast comprising: a body containing a thermoplastic resin material and being in the form of a sheet wrapped in a roll, said roll adapted to be immersed in hot water to prepare the resin material for wrapping onto a limb or body part of a patient; and a quantity of (poly)ethylene oxide applied to the body to prevent adherence of adjacent convolutions of the roll.

2. An assembly as set forth in claim 1, wherein the (poly)ethylene oxide is in the form of a layer on the outer surface of the body.

3. An assembly as set forth in claim 1, wherein said (poly)ethylene oxide is in the resin of said body.

4. An assembly as set forth in claim 1, wherein the (poly)ethylene oxide is applied to the body from a water solution.

5. An assembly as set forth in claim 1, wherein the (poly)ethylene oxide is applied to the body from a chlorinated solvent solution.

6. An assembly as set forth in claim 1, wherein the quantity of (poly)ethylene oxide is in the form of a coating on the outer surface of the body.

7. The method of preparing an orthopedic cast material containing a thermoplastic resin comprising: providing a length of said cast material; and applying (poly)ethylene oxide to the said length of material to prevent adjacent convolutions of the layer from adhering to each other when the length is in the form of a roll.

8. A method as set forth in claim 7, wherein said applying step includes immersing the cast material in a solvent solution of the (poly)ethylene oxide.

9. A method as set forth in claim 8, wherein the solvent is water.

10. A method as set forth in claim 9, wherein said solution contains 0.01% to 0.5% (poly)ethylene oxide.

11. A method as set forth in claim 9, wherein said solutions contains 0.09% (poly)ethylene oxide.

12. A method as set forth in claim 8, wherein the solvent is a chlorinated solvent.

13. A method as set forth in claim 7, wherein said applying step includes spraying the (poly)ethylene oxide on the cast material.

14. A method as set forth in claim 7, wherein said applying step includes coating the surface of the cast material with (poly)ethylene oxide.

15. A method as set forth in claim 7, wherein said applying step includes adding (poly)ethylene oxide to the resin of said cast material.

16. A method as set forth in claim 15, wherein the (poly)ethylene oxide is approximately 1% by weight of the resin in said cast material.

17. A method as set forth in claim 7, wherein said applying step includes adding (poly)ethylene oxide to the resin of said cast material and coating the surface of the cast material with (poly)ethylene oxide.

* * * * *